United States Patent
Nickel et al.

(10) Patent No.: US 6,616,859 B1
(45) Date of Patent: Sep. 9, 2003

(54) PREPARATION OF ALCOHOLIC SOLUTIONS OF ALKALI METAL ALKOXIDES

(75) Inventors: Uwe Nickel, Bad Homburg (DE); Leonhard Unverdorben, Nidderau (DE); Joachim Weber, Frankfurt am Main (DE); Erwin Dietz, Königstein (DE); Juergen Patzlaff, Rossdorf (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 09/879,747

(22) Filed: Jun. 11, 2001

(30) Foreign Application Priority Data

Jun. 9, 2000 (DE) .......................................... 100 28 754

(51) Int. Cl.$^7$ .............................. C09K 3/00; C07C 31/30
(52) U.S. Cl. .................................... 252/182.12; 568/851
(58) Field of Search ...................... 252/182.12; 568/851

(56) References Cited

U.S. PATENT DOCUMENTS

| 3,971,833 | A | 7/1976 | Lenz et al. |
| 4,150,244 | A | 4/1979 | Knorre et al. |
| 4,709,103 | A | 11/1987 | Surber |
| 5,534,328 | A | 7/1996 | Ashmead et al. |
| 5,811,062 | A | 9/1998 | Wegeng et al. |
| 6,437,104 | B1 | 8/2002 | Nickel et al. ............... 534/582 |
| 6,469,147 | B2 | 10/2002 | Nickel et al. ............... 534/582 |

FOREIGN PATENT DOCUMENTS

| DE | 39 26 466 | 2/1991 |
| EP | 0 749 947 | 10/1998 |
| WO | 99/65849 | 12/1999 |

Primary Examiner—Matthew A. Thexton
(74) Attorney, Agent, or Firm—Anthony A. Bisulca

(57) ABSTRACT

A process for preparing alcoholic solutions of alkali metal alkoxides. The process includes reacting an alkali metal with an alcohol in a microreactor wherein the microreactor provides laminer flow.

11 Claims, 1 Drawing Sheet

PREPARATION OF ALCOHOLIC SOLUTIONS OF ALKALI METAL ALKOXIDES

BACKGROUND OF THE INVENTION

The present invention describes a process for preparing alcoholic solutions of alkali metal alkoxides in microreactors.

Alkali metal alkoxides are very important as intermediates, reactants and catalysts in the synthesis of many organic compounds. Various processes are known for making them.

The alkali metal alkoxides of tertiary alcohols have wakened growing interests for use as catalysts and condensation agents, since the associated alcohols are sterically hindered, have low acidity and hence are stronger proton acceptors and substantially less prone to side reactions than primary or secondary alcohols. In many cases the alkoxides are used in the form of their solutions in the corresponding alcohol. The alcohol can also act as a solvent in the desired reaction, so that the number of solvents used can be reduced, providing economical processes involving less equipment. In addition, in the form of their solutions the alkoxides are substantially less problematical to handle on an industrial scale than in solid form.

One of the ways to prepare alkoxides is to react the free alkali metal with the alcohol directly. It is known, for example from DE-A-26 12 642, that the reaction slows with increasing chain length of the alcohol and also increasing degree of branching: primary alcohols give the fastest reaction, tertiaries the slowest. Various specific processes for preparing alkoxides are known from the literature.

DE-A-23 33 634, DE-A-26 12 642 and EP-A-0 749 947 disclose processes for preparing alcohol-free alkali metal alkoxides in an inert solvent by batchwise reaction of the alkali metal with the alcohol. DE-A-23 33 634 utilizes elevated temperature and pressure to speed the reaction, while DE-A-26 12 642 and EP-A-0 749 947 utilize the sodium metal in finely divided form. However, all these processes have the disadvantage that an additional inert solvent is used. To obtain an alcoholic solution of the alkali metal alkoxide, this inert solvent must first be removed again completely and the solid alkoxide obtained redissolved in the alcohol. This creates additional costs, more equipment is needed and process times lengthened.

EP-A-0 192 608 discloses a batch process for preparing alcoholic solutions of alkali metal tert-alkoxides by reacting an alkali metal with a tertiary alcohol by adding the hot alcohol to the molten alkali metal while stirring with an anchor or blade agitator. Again, the reaction takes hours. Moreover, alcohols having boiling points below the melting point of the alkali metal used cannot be reacted at a sufficient rate, since the solid alkali metal cannot be adequately dispersed in the solvent.

WO 99/65849 discloses a batch process for preparing solid alkali metal alkoxides in the presence of a catalyst which, however, is not removed thereafter.

A feature common to these processes is the relatively large amount of alkali metal which has to be used all at once and which is contacted with alcohol, so that substantial amounts of hydrogen are also formed within a short time. This leads to high safety requirements on an industrial scale. To obtain economically sensible reaction times, the fine division of the alkali metal is decisive, and it is usually obtained by intensive mechanical dispersion. Similarly, taking processes from the laboratory scale to the large industrial scale is inconvenient with batch processes and can present problems, since for example vessel and stirrer geometries or heat transfers have a substantial effect on reaction times and conversion rates, for example.

It is an object of the present invention to provide a process for economical, technically reliable and rapid preparation of alcoholic solutions of alkali metal alkoxides that leads to economical reaction times and satisfactory production scale processes even in the case of higher and branched alcohols in that scale-up is simple to accomplish and the process safety risk can be minimized, for example by minimizing the amount of alkali metal added per reactor volume.

It is known to conduct certain chemical reactions in microreactors. Microreactors are constructed from stacks of grooved plates and described in DE 39 26 466 C2, U.S. Pat. No. 5,534,328 and U.S. Pat. No. 5,811,062.

SUMMARY OF THE INVENTION

It has now been found that, surprisingly, microreactors are useful for preparing alcoholic solutions of alkali metal alkoxides.

As used herein, the term "microreactor" is representative of micro- and minireactors, which differ only by reasons of the dimensions and construction of the reaction channel structures. It is possible to use, for example, microreactors as known from the cited references or from publications of the Institut für Mikrotechnik Mainz GmbH, Germany, or else commercially available microreactors, for example Selecto™ based on Cytos™ from Cellular Process Chemistry GmbH, Frankfurt/Main.

The invention accordingly provides a process for preparing alcoholic solutions of alkali metal alkoxides, which comprises reacting an alkali metal with an alcohol in a microreactor.

DESCRIPTION OF THE PREFERRED EMBODIMENTS

Figure 1:
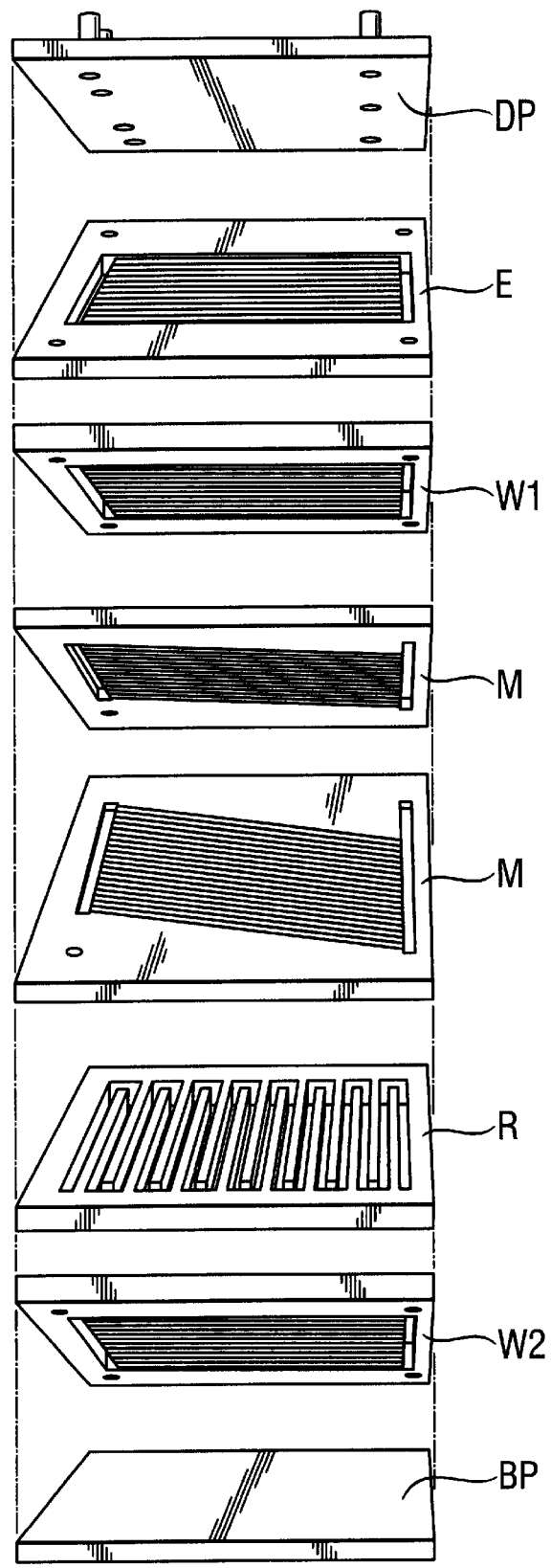
FIG. 1 is a exploded view of the microreactor system.

In the process of the invention, the alkali metal and the alcohol are fed to the microreactor in liquid or molten form and continuously mixed with each other and reacted in the microreactor. Instead of the pure alcohol it is also possible to use an alcoholic solution of an alkali metal alkoxide of low concentration and are concentrated by reaction with the alkali metal in the microreactor. Similarly, the alkoxide solution formed can be recycled. In what follows, the two reactant feeds, the alkali metal and the alcohol/alkoxide solution, are referred to as streams.

The hydrogen formed is advantageously discharged from degassing zones.

Similarly, the auxiliaries used in the conventional process can be used in the process of the invention.

The alkali metals used are preferably lithium, sodium, potassium or lithium, sodium or potassium alloy, preferably sodium or potassium, especially sodium.

The process of the invention is used for preparing alcoholic solutions of alkali metal alkoxides of alcohols of 1 to 30 carbon atoms, preferably 3 to 30 carbon atoms, particularly preferably for secondary, tertiary and branched alcohols of 4 to 30 carbon atoms, especially for sec-butanol, tert-butanol, tert-amyl alcohol, 3,7-dimethyl-1,6-octadien-3-ol (linalool), 3,7,11-trimethyl-3,6,10-dodecatrien-3-ol, 3,7,11,15-tetramethyl-1-hexadecen-3-ol and tetrahydrolinalool. A further preferred use is the preparation of alcoholic solutions of alkali metal alkoxides of relatively long-chain alcohols, for example stearyl alcohol, or of polyhydric alcohols.

The alcohol is used in such an excess over the alkali metal used that the alkoxide formed always remains in solution or there is always a solids-free melt present.

During the reaction, the temperature is advantageously maintained above the melting point of the alkali metal and of the alcohol and above the melting point of the resultant alcoholic solution of alkali metal alkoxide. The temperatures can be between 25° C. and 250° C., preferably between 25° C. and 200° C., especially between 25° C. and 150° C. The reaction can advantageously also be carried out under elevated pressure, for example in the case of alcohols whose boiling point at atmospheric pressure is below or only a little above the melting point of the alkali metal, in order that temperatures above the melting point of the alkali metal may be used and it is not necessary for the reaction to be carried out close to the boiling point of the alcohol. The pressures can be between atmospheric pressure and 100 bar overpressure, preferably between atmospheric pressure and 50 bar, especially between atmospheric pressure and 25 bar.

The concentration of the alkoxide solution prepared is advantageously up to 70% by weight, preferably 5 to 60% by weight, especially 10 to 50% by weight.

A microreactor is constructed from a plurality of laminae which are stacked and bonded together and whose surfaces bear micromechanically created structures which interact to form spaces for chemical reactions. The system contains at least one continuous channel connected to the inlet and the outlet. The flow rates of the streams are limited by the apparatus, for example by the pressures which result depending on the geometry of the microreactor. It is desirable for the reaction to take place completely in the microreactor, but it is also possible to adjoin mixing zones in the form of micromixers and/or delay zones. Similarly, the streams can be repeatedly fed at a plurality of consecutive locations.

The flow rates are advantageously between 0.05 ml/min and 5 l/min, preferably between 0.05 ml/min and 500 ml/min, particularly preferably between 0.05 ml/min and 250 ml/min, especially between 0.1 ml/min and 100 ml/min. The flow rates of the two streams can differ.

A microreactor useful for the elementary steps of preparing alcoholic solutions of alkali metal alkoxides is described in FIG. 1 by way of example. The present microreaction system is in this case constructed from six microstructured metal laminae, stacked and bonded together, plus a lid plate (DP) and a base plate (BP) to form a processing module that is firmly held or bonded together to compress sealing sheets between the plates. The present microreaction system includes two heat exchangers for cooling and/or heating medium, a mixing zone for mixing the reactants and a short delay zone.

The heat exchanger (W1) preheats the streams flowing separately into the plate (E). The streams are then mixed within the plates (M), which form a common space. The delay zone (R) brings the reaction mixture to the aforementioned reaction temperatures with the aid of the heat exchanger (W2), so that the respective reaction can take place.

The microreaction system is preferably operated continuously, and the quantities of material which mixed with each other in each case are in the microliter ($\mu$l) to milliliter (ml) region.

The dimensions of the microstructured regions within the reactor are decisive for the steps of preparing alcoholic solutions of alkali metal alkoxides in a microreaction system. Appropriate geometric styling is used to ensure that there are no dead zones, for example dead ends or sharp corners. Preference is therefore given to continuous paths having round corners. The structures have to be sufficiently small to exploit the intrinsic advantages of microreaction technology, namely excellent heat control, laminar flow, diffuse mixing and low internal volume.

The clear width of the material-ducting channels is advantageously 0.1 to 10 000 $\mu$m, preferably 1 to 2 000 $\mu$m, particularly preferably 1 to 800 $\mu$m, especially 1 to 100 $\mu$m.

The clear width of the heat exchanger channels depends primarily on the clear width of the liquid- or suspension-ducting channels and is advantageously not more than 10 000 $\mu$m, preferably not more than 2 000 $\mu$m, especially not more than 800 $\mu$m. The lower limit for the clear width of the heat exchanger channels is uncritical and is at most constrained by the pressure increase of the heat exchanger fluid to be pumped and by the necessity for optimum heat supply or removal.

The dimensions of a preferred microreaction system, illustrated by way of example in FIG. 1, are:

| Heat exchanger structures: | channel width | ~600 $\mu$m |
|---|---|---|
| | channel height | ~250 $\mu$m |
| Mixer: | channel width | ~600 $\mu$m |
| | channel height | ~500 $\mu$m |

In the microreactor type described by way of example, the six superposed and closely conjoined metal laminae are preferably supplied with all heat exchanger fluids and reactants from above. The product and the heat exchanger fluids are preferably likewise removed upwardly. The flows are preferably controlled via precision piston pumps and a computer-controlled control system. The reaction temperature is monitored via integrated sensors and monitored and controlled with the aid of the control system and a thermostat/cryostat.

The system used here is made of stainless steel; other materials, for example glass, ceramic, silicon, plastics or other metals, may also be used.

It is surprising and was unforeseeable that the production of alcoholic solutions of alkali metal alkoxides would be possible in this technically simple and reliable manner, since it was unforeseeable that the reaction can be carried out without mechanical mixing, i.e., that the mixing that takes place in the microreactor will be sufficient.

The process of the invention requires no further solvents or auxiliaries. This eliminates, for example, the need to work up a second solvent. Nor is it necessary to improve the dispersing and mixing by addition of a surface-active substance, nor is a catalyst required. A further advantage is the relatively low reaction temperature; even temperatures just above the melting point of the alkali metal provide throughputs which are economical and satisfactory on a production scale. Low temperatures also make it possible to minimize unwanted side reactions.

The alcoholic alkali metal alkoxide solutions prepared according to the invention can be used directly for all syntheses requiring alcoholic solutions of alkoxides, especially of secondary and tertiary alkoxides.

EXAMPLES

In the examples which follow, percentages are by weight.

Example 1

518 g of tert-amyl alcohol (boiling point at 2.5 bar: 129° C.) are charged to a feed vessel and circulated with a pump through the microreactor at 120° C. at a flow rate of 30 ml/min. 34.5 g of sodium are then additionally pumped continuously into the microreactor at 103° C. and a flow rate of 0.2 ml/min. The feed vessel, which is sealed pressuretight, is equipped with a cooler which is sealed off from the outside by an overflow valve. The hydrogen formed in the course of the reaction is discharged in a controlled manner via this valve, which opens at a pressure of more than 2.5 bar. The stock reservoir vessel, the reactor, the piping and the pump heads are temperature controlled to 120° C. On completion of the metered addition of sodium, hydrogen evolution has ceased and a 30% solution of sodium tert-amyl oxide and tert-amyl alcohol has formed.

What is claimed is:

1. A process for preparing an alcoholic solution of an alkali metal alkoxide, which comprises reacting an alkali metal with an alcohol in a microreactor, wherein said microreactor provides laminar flow.

2. The process of claim 1, wherein said alkali metal and said alcohol are fed to said microreactor in molten or liquid form and are continuously mixed with each other and reacted in said microreactor.

3. The process of claim 1, wherein said alkali metal is lithium, sodium, potassium or a lithium, sodium or potassium alloy.

4. The process of claim 1, wherein said alcohol is a $C_1$–$C_{30}$-alcohol.

5. The process of claim 1, wherein said alcohol is sec-butanol, tert-butanol, tert-amyl alcohol, 3,7-dimethyl-1,6-octadien-3-ol, 3,7,11-trimethyl-3,6,10-dodecatrien-3-ol, 3,7,11,15-tetramethyl-1-hexadecen-3-ol or tetrahydrolinalool.

6. The process of claim 1, wherein the reaction takes place above the melting point of said alkali metal, of said alcohol and of the resultant solution of said alkali metal alkoxide.

7. The process of claim 1, wherein said reaction is effected between 25 and 250° C., preferably between 25 and 200° C.

8. The process of claim 1, wherein said alkali metal and said alcohol are introduced to said microreactor as liquids and are brought to and held at the reaction temperature in said microreactor by means of one or more heat exchangers.

9. The process of claim 1, wherein said alkali metal and said alcohol are introduced to said microreactor as liquids and pass through said microreactor in a continuous path with rounded corners.

10. The process of claim 1, wherein the concentration, flow rates and temperatures are captured and controlled via sensors and control circuits integrated in said microoreactor.

11. A process for preparing an alcoholic solution of an alkali metal alkoxide, which comprises reacting an alkali metal with an alcohol in a microreactor, wherein said alkali metal and said alcohol are fed to said microreactor in molten or liquid form and are continuously mixed with each other and reacted in said microreactor, and wherein said alkali metal and said alcohol pass through said microreactor in a continuous path with rounded corners.

* * * * *